(12) United States Patent
Van Bladel et al.

(10) Patent No.: US 11,185,414 B2
(45) Date of Patent: *Nov. 30, 2021

(54) SYSTEMS AND METHODS FOR DEPLOYING A CARDIAC ANCHOR

(71) Applicant: BioVentrix, Inc., San Ramon, CA (US)

(72) Inventors: Kevin Van Bladel, Livermore, CA (US); Meir Moshe, El Sobrante, CA (US); Michael S. Dana, Fremont, CA (US)

(73) Assignee: BioVentrix, Inc., San Ramon, CA (US)

( * ) Notice: Subject to any disclaimer, the term of this patent is extended or adjusted under 35 U.S.C. 154(b) by 145 days.

This patent is subject to a terminal disclaimer.

(21) Appl. No.: 16/274,751

(22) Filed: Feb. 13, 2019

(65) Prior Publication Data

US 2019/0307564 A1 Oct. 10, 2019

Related U.S. Application Data

(63) Continuation of application No. 15/259,375, filed on Sep. 8, 2016, now Pat. No. 10,206,779.

(Continued)

(51) Int. Cl.
*A61F 2/24* (2006.01)
*A61B 17/04* (2006.01)
(Continued)

(52) U.S. Cl.
CPC ........ *A61F 2/2487* (2013.01); *A61B 17/0401* (2013.01); *A61M 25/0074* (2013.01);
(Continued)

(58) Field of Classification Search
CPC . A61F 2/2484; A61F 2/2487; A61M 25/0074; A61M 25/0082; A61M 25/0136;
(Continued)

(56) References Cited

U.S. PATENT DOCUMENTS

| 4,007,743 A | 2/1977 | Blake |
|---|---|---|
| 5,295,958 A | 3/1994 | Shturman |

(Continued)

FOREIGN PATENT DOCUMENTS

| EP | 1 078 644 A1 | 2/2001 |
|---|---|---|
| WO | 00/06028 A1 | 2/2000 |

(Continued)

OTHER PUBLICATIONS

Cheng, Y et al. Epicardial catheter-based ventricular reconstruction: a novel therapy for ischaemic heart failure with anteroapical aneurysm. 2013. Interactive Cardiovascular and Thoracic Surgery 17: 915-922.

*Primary Examiner* — John P Lacyk
(74) *Attorney, Agent, or Firm* — Kilpatrick Townsend & Stockton, LLP

(57) ABSTRACT

A heart implant alignment and delivery device includes an elongate body having an opening that is disposed near a distal end of the elongate body. The opening is configured so that a heart implant is positionable within the opening with the heart implant exposed to a surrounding environment and so that the heart implant is substantially aligned with the distal end of the elongate body. The device also includes an implant reposition member, such as a cable, that is releasably coupleable with the heart implant and that is operationally coupled with the elongate body so that a first operation of the implant reposition member causes the heart implant to be retractably deployed from the opening of the elongate body. The first operation of the implant reposition member may be effected via a handle mechanism that is attached to a proximal end of the elongate body.

19 Claims, 10 Drawing Sheets

Related U.S. Application Data

(60) Provisional application No. 62/216,835, filed on Sep. 10, 2015.

(51) Int. Cl.
*A61M 25/00* (2006.01)
*A61M 25/01* (2006.01)
*A61B 17/00* (2006.01)
*A61B 17/34* (2006.01)

(52) U.S. Cl.
CPC .... *A61M 25/0082* (2013.01); *A61M 25/0136* (2013.01); *A61B 17/3468* (2013.01); *A61B 2017/00243* (2013.01); *A61B 2017/00323* (2013.01); *A61B 2017/0409* (2013.01); *A61B 2017/0411* (2013.01); *A61B 2017/0417* (2013.01); *A61B 2017/0464* (2013.01); *A61F 2002/249* (2013.01); *A61M 2025/015* (2013.01)

(58) Field of Classification Search
CPC ............ A61B 17/0401; A61B 17/0057; A61B 2017/00243; A61B 2017/0417; A61B 2017/0464
USPC ............................................ 600/37; 606/213
See application file for complete search history.

(56) References Cited

U.S. PATENT DOCUMENTS

| | | |
|---|---|---|
| 5,336,252 A | 8/1994 | Cohen |
| 5,482,037 A | 1/1996 | Borghi |
| 5,755,697 A | 5/1998 | Jones et al. |
| 5,810,884 A | 9/1998 | Kim |
| 5,830,224 A | 11/1998 | Cohn et al. |
| 5,865,730 A | 2/1999 | Fox et al. |
| 5,961,440 A | 10/1999 | Schweich, Jr. et al. |
| 6,010,476 A | 1/2000 | Saadat |
| 6,045,497 A | 4/2000 | Schweich et al. |
| 6,050,936 A | 4/2000 | Schweich, Jr. et al. |
| 6,059,715 A | 5/2000 | Schweich, Jr. et al. |
| 6,080,182 A | 6/2000 | Shaw et al. |
| 6,125,852 A | 10/2000 | Stevens et al. |
| 6,155,968 A | 12/2000 | Wilk |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,166,684 A | 12/2000 | Yoshikawa et al. |
| 6,258,021 B1 | 7/2001 | Wilk |
| 6,260,552 B1 | 7/2001 | Mortier et al. |
| 6,406,420 B1 | 6/2002 | McCarthy et al. |
| 6,494,825 B1 | 12/2002 | Talpade |
| 6,511,416 B1 | 1/2003 | Green et al. |
| 6,572,529 B2 | 6/2003 | Wilk |
| 6,616,684 B1 | 9/2003 | Vidlund et al. |
| 6,623,508 B2 | 9/2003 | Shaw et al. |
| 6,705,988 B2 | 3/2004 | Spence et al. |
| 6,709,382 B1 | 3/2004 | Horner |
| 6,723,038 B1 | 4/2004 | Schroeder et al. |
| 6,746,471 B2 | 6/2004 | Mortier et al. |
| 6,776,754 B1 | 8/2004 | Wilk |
| 6,808,488 B2 | 10/2004 | Mortier |
| 6,859,662 B2 | 2/2005 | Bombardini |
| 6,890,295 B2 | 5/2005 | Michels et al. |
| 7,146,225 B2 | 12/2006 | Guenst et al. |
| 7,326,177 B2 | 2/2008 | Williamson |
| 7,390,329 B2 | 6/2008 | Westra et al. |
| 7,431,691 B1 | 10/2008 | Wilk |
| 7,637,924 B2 | 12/2009 | Gifford et al. |
| 7,722,523 B2 | 5/2010 | Mortier et al. |
| 7,753,923 B2 | 7/2010 | St. Goar et al. |
| 7,766,816 B2 | 8/2010 | Chin et al. |
| 7,785,248 B2 | 8/2010 | Annest et al. |
| 7,942,854 B1 | 5/2011 | Von Oepen et al. |
| 8,066,766 B2 | 11/2011 | To et al. |
| 8,123,668 B2 | 2/2012 | Annest et al. |
| 8,268,009 B2 | 9/2012 | Teitelbaum et al. |
| 8,394,008 B2 | 3/2013 | Annest et al. |
| 8,425,402 B2 | 4/2013 | Annest et al. |
| 8,449,442 B2 | 5/2013 | Annest et al. |
| 8,491,455 B2 | 7/2013 | Annest et al. |
| 8,506,474 B2 | 8/2013 | Chin et al. |
| 8,636,639 B2 | 1/2014 | Annest et al. |
| 8,968,175 B2 | 3/2015 | Annest et al. |
| 8,979,750 B2 | 3/2015 | Bladel et al. |
| 8,986,189 B2 | 3/2015 | Chin et al. |
| 9,039,594 B2 | 5/2015 | Annest et al. |
| 9,044,231 B2 | 6/2015 | Annest et al. |
| 9,095,363 B2 | 8/2015 | Bladel et al. |
| 9,119,720 B2 | 9/2015 | Chin et al. |
| 9,173,711 B2 | 11/2015 | Butler et al. |
| 9,173,712 B2 | 11/2015 | Annest et al. |
| 9,211,115 B2 | 12/2015 | Annest et al. |
| 9,259,319 B2 | 2/2016 | Chin et al. |
| 9,402,722 B2 | 8/2016 | Annest et al. |
| 9,486,206 B2 | 11/2016 | Annest et al. |
| 9,526,618 B2 | 12/2016 | Chin et al. |
| 10,206,779 B2 | 2/2019 | Van Bladel et al. |
| 2001/0025171 A1 | 9/2001 | Mortier et al. |
| 2001/0041821 A1 | 11/2001 | Wilk |
| 2002/0058855 A1 | 5/2002 | Schweich, Jr. et al. |
| 2002/0077524 A1 | 6/2002 | Schweich, Jr. et al. |
| 2002/0077655 A1 | 6/2002 | Frova |
| 2002/0120298 A1 | 8/2002 | Kramer et al. |
| 2002/0123768 A1 | 9/2002 | Gilkerson et al. |
| 2002/0169359 A1 | 11/2002 | McCarthy et al. |
| 2002/0169360 A1 | 11/2002 | Taylor et al. |
| 2002/0188170 A1 | 12/2002 | Santamore et al. |
| 2002/0198563 A1 | 12/2002 | Gainor et al. |
| 2003/0032979 A1 | 2/2003 | Mortier et al. |
| 2003/0163165 A1 | 8/2003 | Bornzin et al. |
| 2003/0166992 A1 | 9/2003 | Schweich, Jr. et al. |
| 2003/0181928 A1 | 9/2003 | Vidlund et al. |
| 2003/0181951 A1 | 9/2003 | Cates |
| 2003/0220587 A1 | 11/2003 | Swenson |
| 2003/0233022 A1 | 12/2003 | Vidlund et al. |
| 2004/0064143 A1 | 4/2004 | Hicken et al. |
| 2004/0082837 A1 | 4/2004 | Willis |
| 2004/0088035 A1 | 5/2004 | Guenst et al. |
| 2004/0138526 A1 | 7/2004 | Guenst |
| 2004/0167374 A1 | 8/2004 | Schweich |
| 2004/0167580 A1 | 8/2004 | Mann et al. |
| 2004/0225304 A1 | 11/2004 | Vidlund et al. |
| 2004/0267306 A1 | 12/2004 | Blaeser et al. |
| 2005/0065506 A1 | 3/2005 | Phan |
| 2005/0075723 A1 | 4/2005 | Schroeder et al. |
| 2005/0096498 A1 | 5/2005 | Houser et al. |
| 2005/0137688 A1 | 6/2005 | Salahieh et al. |
| 2005/0143620 A1 | 6/2005 | Mortier et al. |
| 2005/0149115 A1 | 7/2005 | Roue et al. |
| 2005/0192599 A1 | 9/2005 | Demarais |
| 2005/0215851 A1 | 9/2005 | Kim et al. |
| 2005/0288613 A1 | 12/2005 | Heil, Jr. |
| 2006/0004408 A1 | 1/2006 | Morris et al. |
| 2006/0079736 A1 | 4/2006 | Chin et al. |
| 2006/0131238 A1 | 6/2006 | Belfort et al. |
| 2006/0135962 A1 | 6/2006 | Kick et al. |
| 2006/0161040 A1 | 7/2006 | McCarthy et al. |
| 2006/0161238 A1 | 7/2006 | Hall |
| 2006/0167416 A1 | 7/2006 | Mathis et al. |
| 2006/0178550 A1 | 8/2006 | Jenson |
| 2006/0200002 A1 | 9/2006 | Guenst |
| 2006/0241340 A1 | 10/2006 | Schroeder et al. |
| 2006/0247672 A1 | 11/2006 | Vidlund et al. |
| 2006/0276684 A1 | 12/2006 | Speziali |
| 2007/0005018 A1 | 1/2007 | Tkebuchava |
| 2007/0010876 A1 | 1/2007 | Salahieh et al. |
| 2007/0049971 A1 | 3/2007 | Chin et al. |
| 2007/0055303 A1 | 3/2007 | Vidlund et al. |
| 2007/0073274 A1 | 3/2007 | Chin et al. |
| 2007/0112244 A1 | 5/2007 | McCarthy et al. |
| 2007/0161846 A1 | 7/2007 | Nikotic et al. |
| 2007/0203503 A1 | 8/2007 | Salahieh et al. |

(56) References Cited

U.S. PATENT DOCUMENTS

| | | |
|---|---|---|
| 2007/0265658 A1 | 11/2007 | Nelson et al. |
| 2007/0287884 A1 | 12/2007 | Schena |
| 2008/0058650 A1 | 3/2008 | Saadat et al. |
| 2008/0082132 A1 | 4/2008 | Annest et al. |
| 2008/0097148 A1 | 4/2008 | Chin et al. |
| 2008/0234717 A1 | 9/2008 | Bruszewski |
| 2008/0269551 A1 | 10/2008 | Annest et al. |
| 2008/0294251 A1 | 11/2008 | Annest et al. |
| 2009/0093670 A1 | 4/2009 | Annest et al. |
| 2009/0270980 A1 | 10/2009 | Schroeder et al. |
| 2009/0287165 A1 | 11/2009 | Drapeau et al. |
| 2009/0287304 A1 | 11/2009 | Dahlgren et al. |
| 2010/0010538 A1 | 1/2010 | Juravic et al. |
| 2010/0016655 A1 | 1/2010 | Annest et al. |
| 2010/0057000 A1 | 3/2010 | Melsheimer et al. |
| 2010/0268020 A1 | 10/2010 | Chin et al. |
| 2011/0093007 A1 | 4/2011 | Abbott et al. |
| 2011/0160750 A1 | 6/2011 | Annest et al. |
| 2011/0270191 A1 | 11/2011 | Paul et al. |
| 2012/0190958 A1 | 7/2012 | Annest et al. |
| 2013/0090523 A1 | 4/2013 | Van Bladel et al. |
| 2013/0090672 A1 | 4/2013 | Butler et al. |
| 2013/0090684 A1 | 4/2013 | Van Bladel et al. |
| 2013/0096579 A1 | 4/2013 | Annest et al. |
| 2013/0324787 A1 | 12/2013 | Chin et al. |
| 2013/0325041 A1 | 12/2013 | Annest et al. |
| 2014/0031613 A1 | 1/2014 | Annest et al. |
| 2014/0051916 A1 | 2/2014 | Chin et al. |
| 2014/0330296 A1 | 11/2014 | Annest et al. |
| 2014/0350417 A1 | 11/2014 | Bladel et al. |
| 2015/0066082 A1 | 3/2015 | Moshe et al. |
| 2015/0066139 A1 | 3/2015 | Bladel et al. |
| 2015/0238182 A1 | 8/2015 | Annest et al. |
| 2016/0022422 A1 | 1/2016 | Annest et al. |
| 2016/0030026 A1 | 2/2016 | Bladel et al. |
| 2016/0089132 A1 | 3/2016 | Butler et al. |
| 2016/0095600 A1 | 4/2016 | Annest et al. |
| 2016/0120648 A1 | 5/2016 | Chin et al. |
| 2016/0206427 A1 | 7/2016 | Annest et al. |
| 2016/0262891 A1 | 9/2016 | Chin et al. |
| 2016/0338835 A1 | 11/2016 | Bladel et al. |

FOREIGN PATENT DOCUMENTS

| | | |
|---|---|---|
| WO | 2002/30335 A2 | 4/2002 |
| WO | 2003/032818 A3 | 4/2003 |
| WO | 2004-043267 A2 | 5/2004 |
| WO | 2005/092203 A1 | 10/2005 |
| WO | 2006/044467 A2 | 4/2006 |
| WO | 2007/022519 A2 | 2/2007 |
| WO | 2013-049761 A1 | 4/2013 | ental effects of congestive heart failure, such as by dilating expanding blood vessels, improving and/or increasing pumping of the remaining healthy heart tissue, increasing the elimination of waste fluids, and the like.

SYSTEMS AND METHODS FOR DEPLOYING A CARDIAC ANCHOR

CROSS-REFERENCE TO RELATED APPLICATIONS

This application is a continuation of U.S. patent application Ser. No. 15/259,375 filed Sep. 8, 2016, entitled "Systems and Methods for Deploying a Cardiac Anchor," which claims priority to U.S. Patent Application No. 62/216,835 filed Sep. 10, 2015, entitled "Systems and Methods for Deploying a Cardiac Anchor," the entire disclosures of which are hereby incorporated by reference, for all purposes, as if fully set forth herein.

BACKGROUND

Heart implants are currently used to resize or alter the geometry of a ventricle in a failing heart, such as by reducing its radius of curvature through the process of excluding a portion of the circumference from contact with blood, and thereby reduce wall stress on the heart and improve the heart's pumping performance. Congestive heart failure may, for example, be treated using one or more implants which are selectively positioned relative to a first wall of the heart (typically an interventricular septum), and another wall of the heart so as to exclude scar tissue and limit a cross sectional area, or distance across a ventricle. Functional deterioration of the heart tissues may be inhibited by decreasing a size of the heart chamber and/or approximating tissues so that stress on the tissues is limited.

Congestive heart failure (sometimes referred to as "CHF" or "heart failure") is a condition in which the heart does not pump enough blood to the body's other organs. Congestive heart failure may in some cases result from narrowing of the arteries that supply blood to the heart muscle, high blood pressure, heart valve dysfunction due to degenerative processes or other causes, cardiomyopathy (a primary disease of the heart muscle itself), congenital heart defects, infections of the heart tissues, and the like. However, in many cases congestive heart failure may be triggered by a heart attack or myocardial infarction. Heart attacks can cause scar tissue that interferes with the heart muscle's healthy function, and that scar tissue can progressively replace more and more of the contractile heart tissue. More specifically, the presence of the scar may lead to a compensatory neuro-hormonal response by the remaining, non-infarcted myocardium leading to progressive dysfunction and worsening failure.

People with heart failure may have difficulty exerting themselves, often becoming short of breath, tired, and the like. As blood flow out of the heart decreases, pressure within the heart increases. Not only does overall body fluid volume increase, but higher intracardiac pressure inhibits blood return to the heart through the vascular system. The increased overall volume and higher intracardiac pressures result in congestion in the tissues. Edema or swelling may occur in the legs and ankles, as well as other parts of the body. Fluid may also collect in the lungs, interfering with breathing (especially when lying down). Congestive heart failure may also be associated with a decrease in the ability of the kidneys to remove sodium and water, and the fluid buildup may be sufficient to cause substantial weight gain. With progression of the disease, this destructive sequence of events can cause the progressive deterioration and eventual failure of the remaining functional heart muscle.

Treatments for congestive heart failure may involve rest, dietary changes, and modified daily activities. Various drugs may also be used to alleviate detrimental effects of congestive heart failure, such as by dilating expanding blood vessels, improving and/or increasing pumping of the remaining healthy heart tissue, increasing the elimination of waste fluids, and the like.

Surgical interventions have also been applied for treatment of congestive heart failure. If the heart failure is related to an abnormal heart valve, the valve may be surgically replaced or repaired. Techniques also exist for exclusion of the scar and volume reduction of the ventricle. These techniques may involve (for example) surgical left ventricular reconstruction, ventricular restoration, the Dor procedure, and the like. If the heart becomes sufficiently damaged, even more drastic surgery may be considered. For example, a heart transplant may be the most viable option for some patients. These surgical therapies can be at least partially effective, but typically involve substantial patient risk. While people with mild or moderate congestive heart failure may benefit from these known techniques to alleviate the symptoms and/or slow the progression of the disease, less traumatic, and therefore, less risky therapies which significantly improve the heart function and extend life of congestive heart failure patients has remained a goal.

It has been proposed that an insert or implant be used to reduce ventricular volume of patients with congestive heart failure. With congestive heart failure, the left ventricle often dilates or increases in size. This can result in a significant increase in wall tension and stress. With disease progression, the volume within the left ventricle gradually increases and blood flow gradually decreases, with scar tissue often taking up a greater and greater portion of the ventricle wall. By implanting a device which brings opposed walls of the ventricle into contact with one another, a portion of the ventricle may be excluded or closed off. By reducing the overall size of the ventricle, particularly by reducing the portion of the functioning ventricle chamber defined by scar tissue, the heart function may be significantly increased and the effects of disease progression at least temporarily reversed, halted, and/or slowed.

BRIEF DESCRIPTION

The embodiments described herein are particularly useful for positioning anchors or heart implants against heart walls. According to one aspect, a catheter for delivering and aligning a heart implant about a wall of a heart is provided. The catheter includes an elongate catheter body having a lumen disposed there through and a handle mechanism that is disposed at a proximal end of the elongate catheter body. The elongate catheter body includes a cavity that is positioned near a distal end of the elongate catheter body. The cavity is configured to deliver a heart implant adjacent the wall and is configured to receive the heart implant in a manner such that at least a portion of the heart implant is exposed to an interior region of the heart. A cable is positioned within the lumen of the elongate catheter body. The cable is releasably coupled with the heart implant that is positioned within the cavity and is operationally coupled with the handle mechanism so that a first operation of the handle mechanism causes the cable to flex outward from the cavity, which causes at least part of the heart implant to move outward from the cavity.

The catheter may be further configured so that a second operation of the handle mechanism causes the cable to retract within the lumen of the elongate catheter body, thereby enabling the heart implant to be repositioned within the cavity. The catheter may be even further configured so that a third operation of the handle mechanism causes the cable to retract within the lumen of the elongate catheter body thereby enabling the heart implant to be released from the cavity. The heart implant may be pivotably coupled with a tension member.

A distal tip of the elongate catheter body may be plugged, capped, solid, or otherwise closed so that the lumen does not extend through the distal tip. A distal end of the cable may contact the distal tip of the elongate catheter body so that distal sliding of the cable within the lumen causes the cable to flex outward from the cavity. The cavity may be formed in the distal end of the elongate catheter body by removing more with more than ½ of the material of the elongate catheter body. A strip of material may connect a proximal portion and a distal portion of the elongate catheter body on opposite sides of the cavity. The cable may be slidably disposed through a lumen of the heart implant in order to couple the heart implant with the cavity and elongate catheter body. The distal end of the elongate catheter body may flex or bend in response to the first operation of the handle mechanism and the heart implant may pivot outward from the cavity in response to the first operation of the handle mechanism.

According to another aspect, a heart implant alignment and delivery device is provided. The device includes an elongate body and an opening in the elongate body that is disposed near a distal end of the elongate body. The opening is configured so that a heart implant is positionable within the opening with the heart implant exposed to a surrounding environment, and so that the heart implant is substantially aligned with the distal end of the elongate body. The device also includes an implant reposition member that is releasably coupleable with the heart implant and that is operationally coupled with the elongate body so that a first operation of the implant reposition member causes the heart implant to be retractably deployed from the opening of the elongate body. Retractably deploying the heart implant may involve pivoting the heart implant out of the opening of the elongate body.

The implant reposition member may be also configured so that a second operation of the implant reposition member causes the heart implant to be retracted into the opening with the heart implant substantially aligned or realigned with the distal end of the elongate body. The implant reposition member may be further configured so that a third operation of the implant reposition member causes the heart implant to be permanently deployed from the opening of the elongate body. The device may include a handle mechanism that is disposed at a proximal end of the elongate body. The handle mechanism may be operably coupled with the implant reposition member to effect the first operation, the second operation, and/or the third operation of the implant reposition member. The implant reposition member may be a cable that is slidably disposed within a lumen of the elongate body and the elongate body may be configured so that the distal sliding of the cable within the lumen of the elongate body causes a portion of the cable to protrude outwardly from the opening.

According to another aspect, a method of deploying a heart implant from a catheter is provided. The catheter includes an elongate body having a lumen and a cavity, a cable disposed within the lumen, and a handle mechanism disposed at a proximal end of the elongate body. The heart implant is positioned within the cavity of the elongate body. The method includes positioning a distal end of the elongate body within a chamber of a heart so that the cavity and heart implant are adjacent a wall of the heart and performing a first operation via the handle mechanism to cause the cable to flex outward from the cavity of the elongate body and thereby cause the heart implant to pivot out of the cavity of the elongate body and into contact with the wall. The catheter is configured so that the heart implant is retractable within the cavity to enable repositioning of the elongate body within the heart and thereby ensure a proper alignment of the heart implant relative to the wall of the heart.

The method may also include performing a second operation via the handle mechanism to cause the cable to retract within the lumen of the elongate body and thereby cause the heart implant to retract into the cavity. The cavity and heart implant may then be repositioned within the cavity of the heart after retraction of the cable and heart implant. The method may additionally include repositioning the cavity and heart implant within the chamber of the heart so that the heart implant is repositioned relative to the wall. The first operation of the handle mechanism may then be performed again to cause the cable to flex outward from the cavity and thereby cause the heart implant to pivot out of the cavity and into contact with the wall. The method may additionally include performing a third operation with the handle mechanism to permanently deploy the heart implant from the cavity of the elongate body. The heart implant may be pivotably coupled with a tension member that extend distally from heart implant and through the wall of the heart. The cable may be slidably disposed through a lumen of the heart implant.

BRIEF DESCRIPTION OF THE DRAWINGS

The present invention is described in conjunction with the appended figures.

Figure 1A:
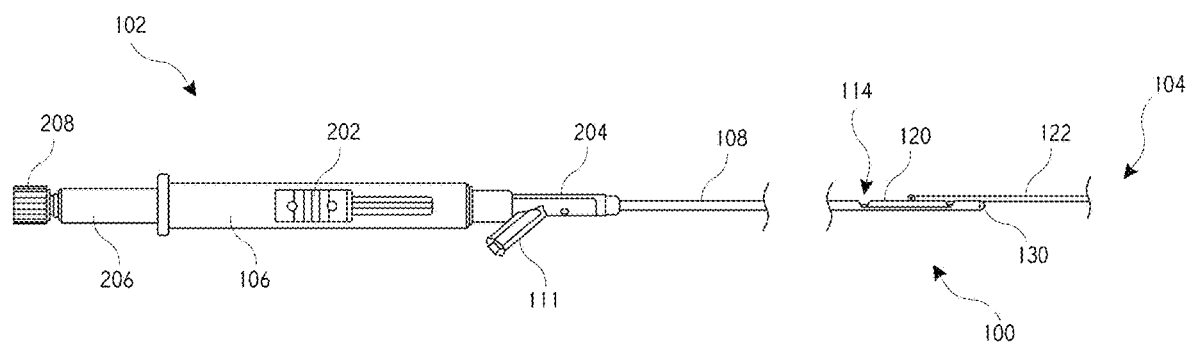
FIGS. 1A-C illustrate various views of a heart implant alignment and delivery device that may be used to deliver, align, and deploy a heart implant within a heart.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

The embodiments herein generally provide improved medical devices, systems, and methods. Exemplary embodiments of the devices are described for use in reducing the distance between a region along the septum and a region of an external wall of the left and/or right ventricle of a heart in a less or minimally invasive manner. Hence, embodiments of the tools and methods described herein may find specific use in the treatment of congestive heart failure and other progressive heart diseases by reconfiguring abnormal heart geometry that may be contributing to heart dysfunction.

The embodiments of the tools and methods described herein are particularly useful for positioning anchors or heart implants that are deployed against the heart walls and that are used to urge opposing heart walls together. The tools and methods allow a physician to have improved control over the position and deployment of the anchor against the heart wall. The improved control enables the physician to ensure that Chordae, Papillary Leaflets, the Tricuspid Valve, and other heart tissue or material are not contacted, entangled, or otherwise detrimentally affected by the heart anchor. The tools and methods also allow the physician to easily reposition the heart anchor if such repositioning is needed. The embodiments herein enable more precise positioning of heart anchors within a chamber of the heart, which may greatly simplify the heart anchor delivery procedure and/or reduce operation and recovery time associated with the procedure.

The controlled placement of the heart anchor is achieved via a catheter or heart implant alignment and delivery device that is configured to deliver the heart anchor within the chamber in a manner that enables the heart anchor to be retractably pivoted or deployed from the catheter. Stated differently, the catheter is designed so that the heart anchor may be deployed from the catheter, but the deployment is controlled so that the heart anchor is not permanently or non-reversibly deployed from the catheter. Rather, the heart anchor remains coupled with the catheter even after an initial deployment, which enables the heart anchor to be retracted against or relative to the catheter if desired.

The retractable deployment of the heart anchor allows a physician to check or inspect a placement, position, or other deployment related characteristic of the heart anchor prior to permanently deploying the heart anchor. For example, the physician may inspect that the heart anchor is properly aligned about the heart, and/or in relation to another heart anchor, to ensure that a desired closure or other treatment of the heart will be achieved via the heart anchor. In other instances, the physician may ensure that the heart anchor is not entangled with or in contact with sensitive heart tissue, such as the Chordae, Papillary Leaflets, Tricuspid Valve, etc. If the physician determines that the heart anchor is not properly aligned about the heart, and/or with another heart anchor, the physician may retract the heart anchor, reposition the heart anchor, and retractably deploy the heart anchor to ensure that a desired and proper alignment and/or placement of the heart anchor is achieved.

After a desired placement or alignment of the heart anchor is achieved, the physician may then permanently deploy the heart anchor from the catheter. The heart anchor may then be used to partially or fully close a portion of the heart as desired. In some instances, retractable deployment of the heart anchor may involve positioning of the heart anchor against one of the walls of the heart, such as adjacent the septum. In other embodiments, the heart anchor may be deployed elsewhere relative to the heart. The physician may inspect the placement or position of the heart anchor via fluoroscopy, echocardiography (e.g., 3D echocardiography, Transesophageal Echocardiography (TEE)), and the like.

The catheter may include an elongate body that includes an opening body that is disposed near a distal end of the elongate body. The elongate body is typically a cylindrical body or tubing. The opening is configured so that a heart implant may be positioned within the opening. The opening is typically formed in a portion of the elongate body by removing some of the tubing's material, which may expose an interior portion of the tubing or elongate body. With the material removed, a small strip or section of the elongate body or tubing may connect a distal and proximal portion of the elongate body.

The heart anchor may be positioned within the opening so that one side of the heart anchor faces the interior of the elongate body. The heart implant is typically exposed to a surrounding environment when positioned within the opening. The heart implant is also typically aligned with the distal end of the elongate body or tubing. The catheter also includes an implant reposition member that is releasably coupled with the heart implant when the heart implant is positioned within the opening. In one embodiment, the implant reposition member is a cable, wire, or cord that is positioned through a lumen of the elongate body and through a lumen of the heart implant. In other embodiments, the implant reposition member may be any component or member that is able to attach to the heart implant in a manner that allows the heart implant to be retractably deployed from the catheter.

The implant reposition member is operationally coupled with the elongate body so that a first operation of the implant reposition member causes the heart implant to be retractably deployed from the opening of the elongate body. The implant reposition member may be attached to a handle mechanism that is disposed at a proximal end of the elongate body and that is operable to effect the first operation of the implant reposition member. Retractable deployment of the heart implant may including pivoting of the heart implant out of the opening of the elongate body.

The implant reposition member is also configured so that a second operation of the implant reposition member causes the heart implant to be retracted into the opening of the elongate body. Upon retraction of the heart implant within the opening, the heart implant is once again substantially aligned with the distal end of the elongate body. The handle mechanism may be designed to effect the second operation of the implant reposition member. The implant reposition member is further configured so that a third operation of the implant reposition member causes the heart implant to be permanently deployed from the opening of the elongate body. The handle mechanism may be designed to effect the third operation of the implant reposition member. In instances where the implant reposition member is a cable, the cable may be slidably disposed within a lumen of the elongate body and the elongate body may be configured so that distal sliding of the cable within the lumen of the elongate body causes a portion of the cable to protrude outwardly from the opening.

Having generally described aspects of a heart implant deliver device or catheter, additional features of such devices will be more apparent in reference to the description of the various figures that is provided below.

Figure 1B:
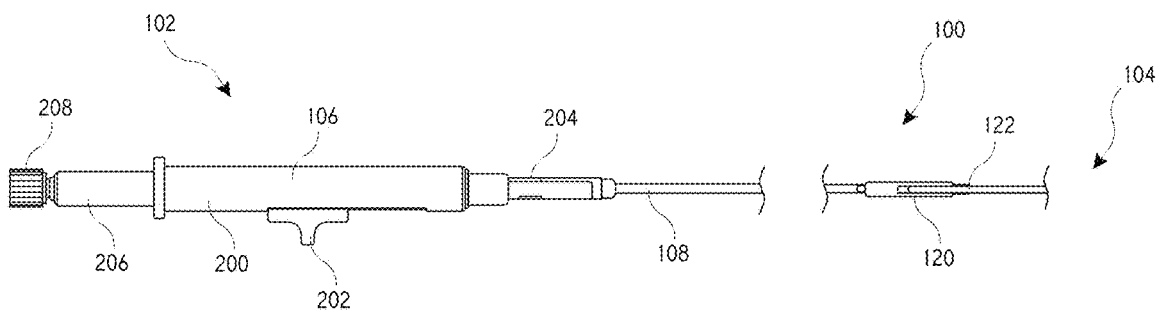
Figure 1C:
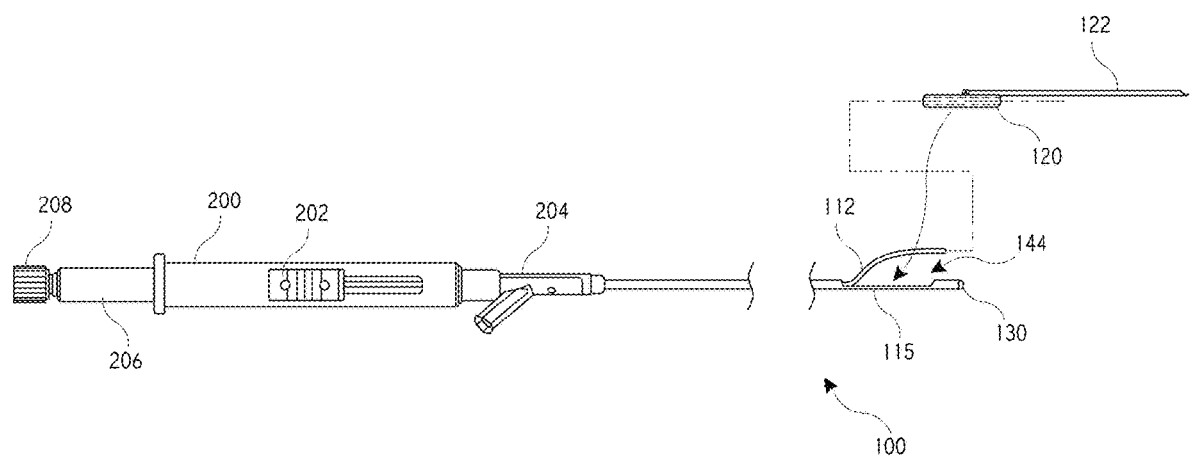

Referring now to the FIGS. 1A-1C, illustrated are various view of a heart implant alignment and delivery device or catheter (hereinafter catheter 100) that may be used to deliver, align, and deploy a heart implant or anchor 120 (hereinafter heart implant 120) within the heart. The catheter 100 has a proximal end 102 and a distal end 104. A handle mechanism 106 (hereinafter handle 106) is attached to the proximal end 102 of the catheter 100. The handle 106 may be used by a physician to control and navigate the distal end 104 of the catheter 100 within the vasculature of a patient's body. Specifically, the distal end 104 may be directed or navigated to a desired location within or adjacent a chamber of the heart for deployment of one or more heart implants 120. The handle 106 is also used in aligning and/or deploying the heart implant 120 within the heart as described in greater detail herein.

The distal end 104 includes an elongate or catheter body 108 (hereinafter elongate body 108) having a lumen 110 (see FIG. 3A) that extends substantially through the elongate body 108. The elongate body 108 is typically a cylindrical body or section of flexible tubing. In some embodiments, the elongate body 108 may be made of a braid material, catheter, or tubing, such as braid reinforced tubing. The elongate body 108 is sufficiently flexible to allow the tubing to be inserted through the vasculature of the patient and within a chamber of the heart. The tubing should be sufficiently flexible and strong to enable insertion within the vasculature while minimizing trauma to the patient. A cable, wire, flexible rod, or other component 112 (hereinafter cable 112) is slidably positioned within the lumen 110 of the elongate body 108. As illustrated in greater detail in FIGS. 2A-C, the cable 112 is operationally coupled with the handle 106 so that an operation of the handle 106 causes the cable 112 to slide proximally and distally within the lumen 110 of the elongate body 108, which effects deployment or retraction of the heart implant 120. Specifically, as described in greater detail below, a grip member 202 of the handle 106 may be slid proximally and distally about the handle 106 to initially deploy and retract the heart implant 120. A release member 208 may be employed to permanently deploy the heart implant 120 after a proper alignment or positioning of the implant is determined.

An opening or cavity 114 (hereinafter cavity 114) is formed in the distal end 104 of the elongate body 108. The cavity 114 is configured so that the heart implant 120 may be positioned within the cavity 114. The cavity 114 is formed in the distal end 104 of the elongate body 108 by removing some of the tubing's material (typically more than ½ of the material), which exposes an interior portion of the tubing and lumen 110. In some embodiments, the cavity 114 may be formed via laser cutting or machining. Laser cutting may be particularly useful when the elongate body 108 is formed of a braid material, since the laser may prevent or minimize fraying of the braid material As illustrated in FIG. 1C, a small strip or material section 115 of the elongate body 108 connects a distal and proximal portion of the elongate body 108 adjacent the cavity 114. The heart implant 120 is positionable within the cavity 114 of the elongate body 108. When positioned within the cavity 114, an exterior surface of the heart implant 120 is positioned against the elongate body 108, although the heart implant 120 generally remains exposed to a surrounding environment as illustrated. The heart implant 120 is also substantially aligned within the distal end 104 of the elongate body 108 when positioned within the cavity 114.

The heart implant 120 is pivotally coupled or attached to a tether or tension member 122 (hereinafter tether 122). Exemplary heart implants 120 and tethers 122 are further described in the following U.S. applications, the disclosures of which are incorporated by reference herein: U.S. application Ser. No. 13/632,108, filed Sep. 30, 2012, entitled "Over-the-Wire Cardiac Implant Delivery System for Treatment of CHF and Other Condition"; U.S. application Ser. No. 13/632,106, filed Sep. 30, 2012, entitled "Cardiac Implant Migration Inhibiting Systems"; U.S. application Ser. No. 13/632,104, filed Sep. 30, 2012, entitled "Trans-Catheter Ventricular Reconstruction Structures, Methods, and Systems for Treatment of Congestive Heart Failure and Other Conditions"; U.S. application Ser. No. 13/632,103, filed Sep. 30, 2012, entitled "Remote Pericardial Hemostasis for Ventricular Access and Reconstruction or Other Organ Therapies". As described in said applications, the tether 122 may be used to apply tension to the heart walls and/or fix the heart walls in engaged state to close off a portion of a heart chamber. The tether 122 may also be used to guide the heart implant 120 to a desired location within the heart chamber. In such instances, the tether 122 may extend distally of the distal end 104 of the elongate body 108 as illustrated.

The heart implant 120 is coupleable with the elongate body 108 so that the heart anchor 120 may be removed or uncoupled therefrom. For example, FIGS. 1A and 1B illustrate the heart implant 120 positioned within the cavity 114 of the elongate body 108 while FIG. 1C illustrated the heart implant 120 removed therefrom. The heart implant 120 is removably coupled with the cavity 114 by inserting the cable 112 through a lumen 124 of the heart implant 120 as illustrated in greater detail in FIGS. 3A and 3B.

The distal tip of the elongate body 108 is plugged, capped, or otherwise closed so that the cable 112 is not able to extend entirely through the elongate body 108 and beyond the distal tip of the elongate body 108. To plug, cap, or close the distal tip, a cap or plug 130 (hereinafter plug 130) is coupled or attached to the distal tip. Because the distal tip is plugged, capped, or otherwise closed, distal sliding of the cable 112 causes the cable 112 to flex and deploy outward from the cavity 114, which is used in initially deploying the heart implant 120 within the heart chamber.

Figure 2A:
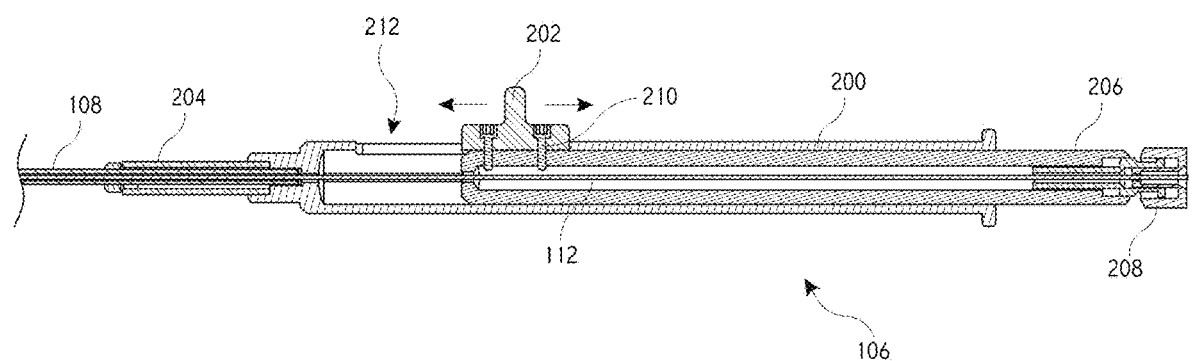
FIGS. 2A-C illustrate cross sectional views of a handle mechanism of the heart implant alignment and delivery device of FIGS. 1A-C.
Figure 2B:
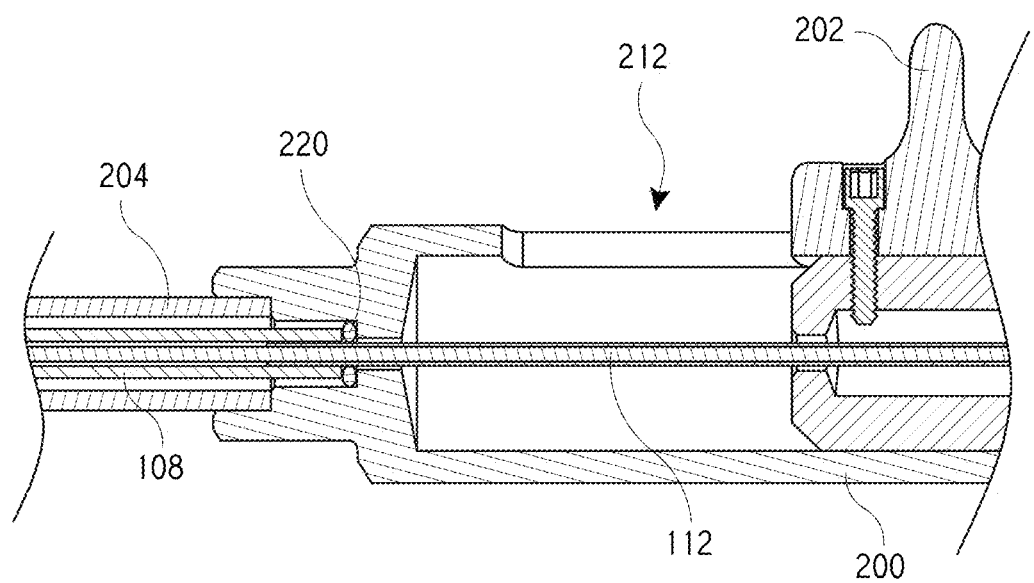
Figure 2C:
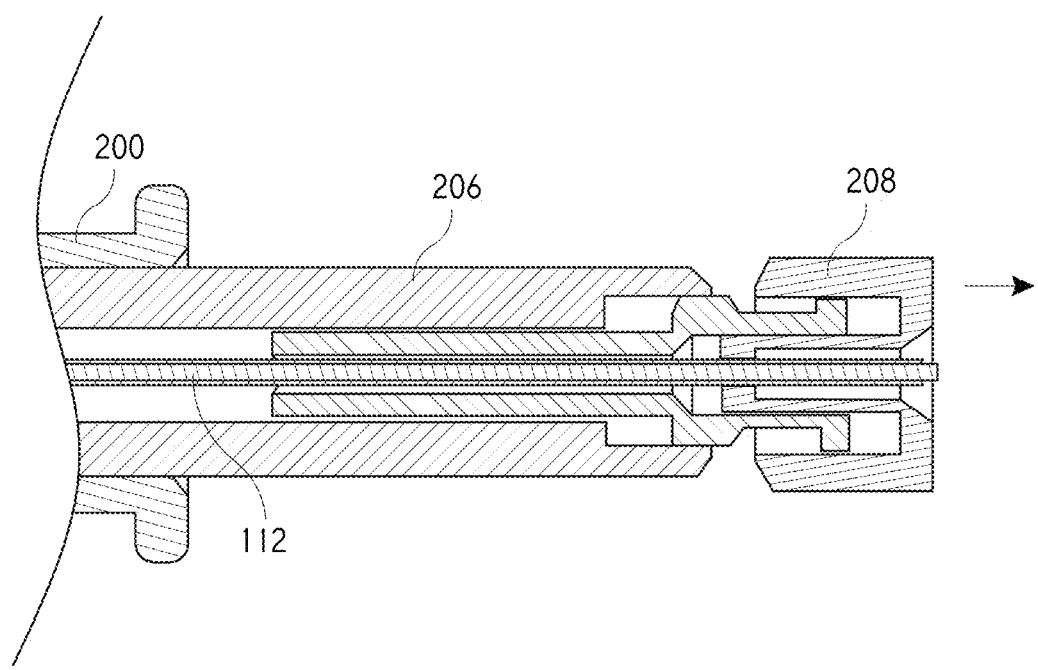

FIGS. 2A-C illustrate cross sectional views of the handle 106 of the catheter 100 in greater detail. The handle 106 is configured to be grasped and manipulated by a physician to align and deploy the heart implant 120 within the heart. FIG. 2A illustrates a cross section of the entire handle 106, while FIGS. 2B and 2C illustrate distal and proximal ends of the handle 106, respectively. As illustrated, the cable 112 is positioned through the lumen 110 of the elongate body 108 and through the interior of the handle 106. The cable 112 is fixedly attached to a plunger 206 that is axially movable or slidable within a main body 200 of the handle 106. The plunger 206 is attached to the grip member or lever 202 (hereinafter grip member 202) so that axial sliding of the grip member 202 causes the plunger 206 to move axially within the main body 200. In turn, axial movement of the plunger 206 causes the cable 112 to similarly move or slide axially within the elongate body 108. The grip member 202 may be mechanically attached to the plunger 206 via set screws 210 or other mechanical fasteners as illustrated. In other embodiments, the grip member 202 may be adhesively bonded, ultrasonically welded, RF welded, and the like to the plunger 206.

The grip member 202 is slidably disposed within a elongate slot or opening 212 of the main body 200. The elongate slot 212 limits the amount of sliding of the grip member 202 relative to the main body 200, which correspondingly limits the amount of axial sliding of the plunger 206 within the main body 200 and thereby limits the amount of axial sliding of the cable 112 within the lumen 110 of the elongate body 108. The catheter 100 may be arranged so that the distal end of the cable 112 is adjacent to, or contacts, the plug 130 when the grip member 202 is positioned at a proximal most point within the elongate slot 212. In such instances, distal sliding of the grip member 202 within the elongate slot 212 causes the cable 112 to flex or deploy outwardly from the cavity 114 since the plug 130 prevents the cable's distal tip from extending or protruding beyond the distal tip of the elongate body 108. In this manner, distal sliding of the grip member 202 may be employed to initially deploy the heart implant 120 from the cavity 114 of the elongate body 108. The grip member 202 may be slid proximally to retract the cable 112 within the cavity 114 of the elongate body 108. In this manner, proximal sliding of the grip member 202 may be employed to retract the heart implant 120 within the cavity of the elongate body 108.

An access member 204 is coupled with the distal end of the main body 200. The access member 204 may couple with the elongate body 108 and reinforce the elongate body 108. The access member 204 may include a port 111 that provides fluid access to the elongate body 108 and/or vasculature. An O-ring 220, or other fluid inhibitor, may be disposed within a distal end of the main body 200 at a proximal end of the elongate body 108. The O-ring 220 may be used to fluidly seal the elongate body 108 in order to prevent blood or other bodily fluid from passing through the elongate body 108 and into the main body 200 of the handle 106. In some instances, the cable 112 may be reinforced within the interior of the main body 200, such as by including a rigid covering or tubing that prevents or minimizes buckling of the cable 112.

A release member or cable deployment mechanism 208 (hereinafter cable deployment mechanism 208) is removably attached to the proximal end of the plunger 206. The cable deployment mechanism 208 is also fixedly attached to the cable 112. The cable deployment mechanism 208 is designed to be removed or detached from the plunger 206 and pulled proximally relative thereto. Detachment of the cable deployment mechanism 208 from the plunger 206, and proximal movement of the cable deployment mechanism 208 relative thereto, causes the cable 112 to be slid proximally within the lumen 110 of the elongate body 108 and out of engagement with the heart implant 120. This allows the heart implant 120 to be permanently deployed or detached from the cavity 114 of the elongate body. The cable deployment mechanism 208 may include a luer type connector, or any other connector, to enable the cable deployment mechanism 208 to be detached from the proximal end of the plunger 206.

In operation, the handle 106 is used to both initially deploy the heart implant 120 and to permanently deploy the heart implant 120 once a desired alignment or orientation of the heart implant is achieved. For example, the heart implant 120 may be inserted within the patient's vasculature and into a chamber of the heart (e.g., left ventricle). The heart implant 120 is typically positioned within the cavity 114 of the elongate body 108 during insertion of the heart implant 120 through the vasculature. Insertion of the heart implant 120 within the vasculature and heart chamber is further described in the various U.S. applications incorporated by reference herein.

The grip member 202 may then be slid distally within the elongate slot 212 to flex the cable 112 outward from the cavity 114, which correspondingly causes the heart implant 120 to pivot or deploy outward from the cavity 114 due to the coupling of the cable 112 and the heart implant 120. A physician may determine if the heart implant 120 is properly aligned or oriented within the heart chamber, or if the heart implant is in contact with any sensitive tissue. If the heart implant 120 is not properly aligned, or if the heart implant 120 contacts sensitive tissue, the grip member 202 may be slid proximally within the elongate slot 212 to retract the heart implant 120 within the cavity of the elongate body 108. The heart implant may then be realigned or repositioned within the heart chamber via proximal or distal movement of the elongate body 108, rotation of the handle 106 and elongate body 108, etc., and the heart implant 120 may then be redeployed within the heart chamber via the grip member 202 to determine if the new alignment or orientation of the heart implant 120 is proper.

Upon a determination of a proper alignment or orientation of the heart implant 120, the cable deployment mechanism 208 may be detached from the plunger to disengage the cable 112 from the heart implant 120, which enables the heart implant 120 to be permanently deployed or detached from the elongate body 108. The heart implant 120 may then be used to apply tension to the heart walls so as to bring opposing heart walls into engagement. The heart implant 120 and tether may then be used to permanently affix the engaged heart walls. Tensioning and affixing of the heart walls is further described in the various U.S. applications incorporated by reference herein.

Figure 3A:
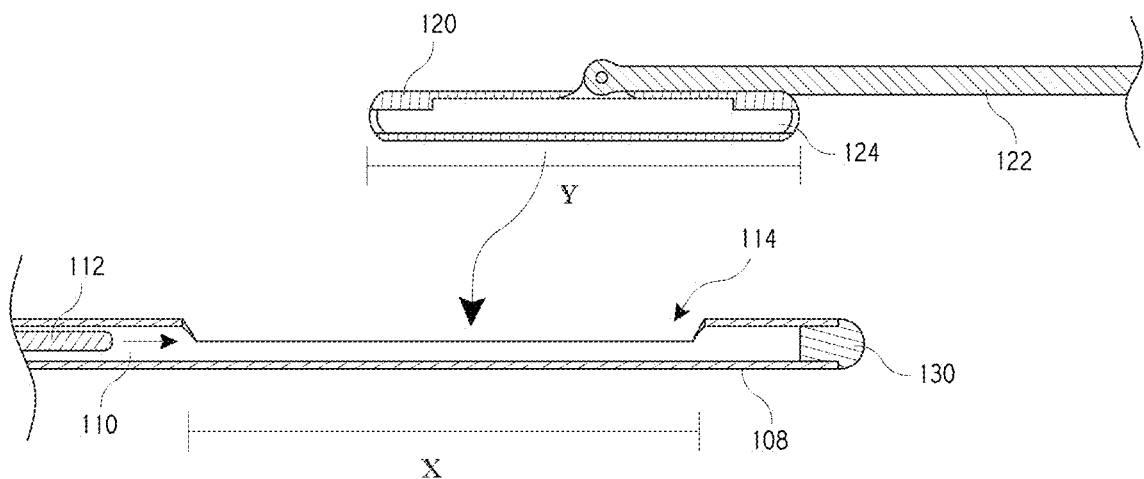
FIGS. 3A-C illustrate cross sectional views of a distal end of the heart implant alignment and delivery device of FIGS. 1A-C.
Figure 3B:
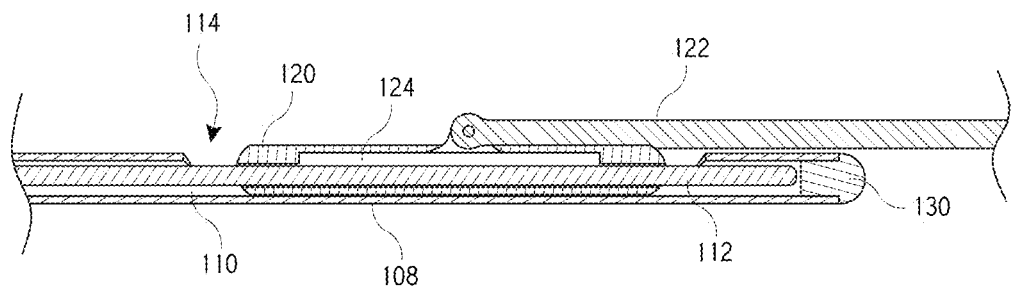
Figure 3C:
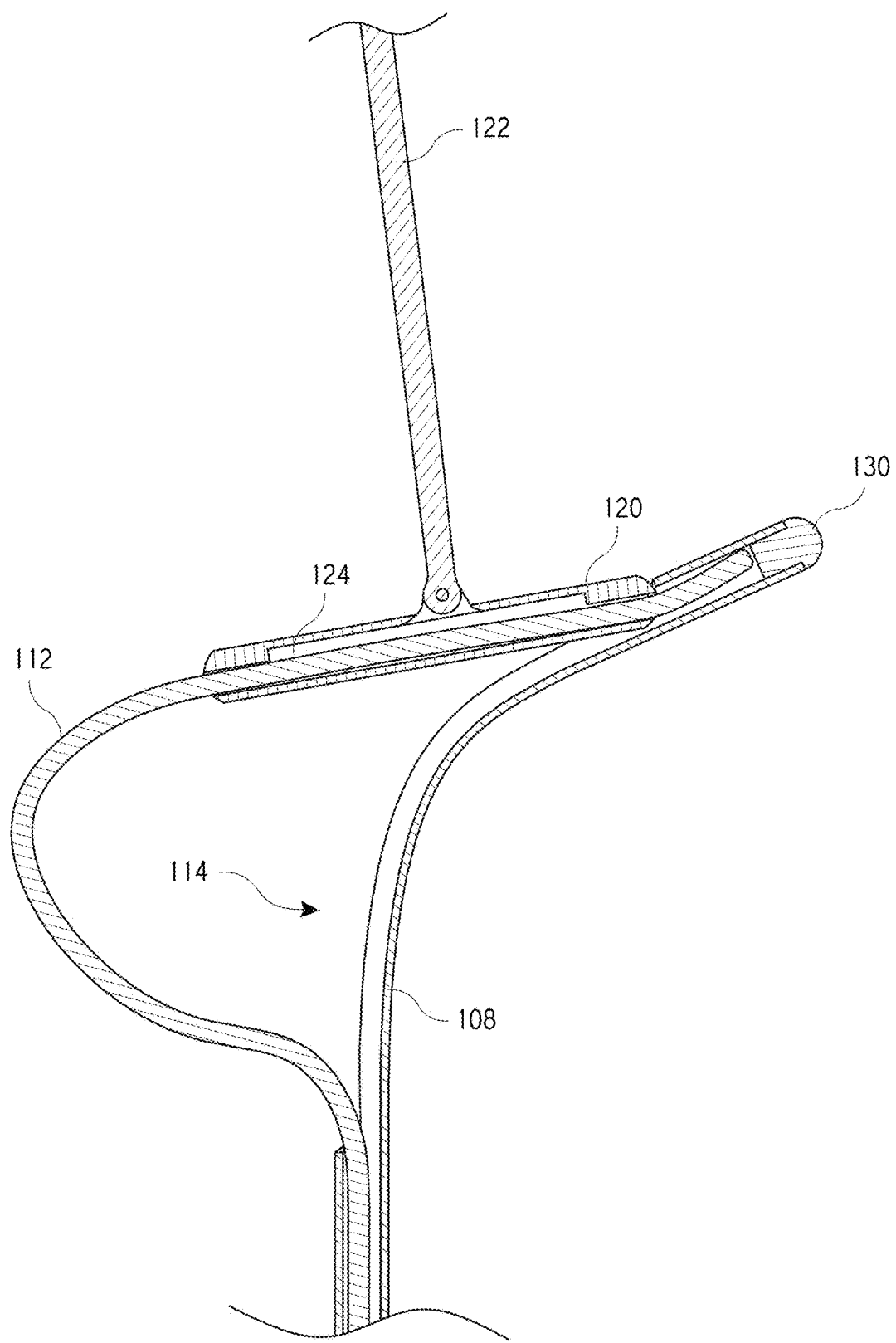

Referring now to FIGS. 3A-C, illustrated are cross sectional views of the distal end 102 of the elongate body 108. FIGS. 3A-C provide greater detail of the functional relationship or operation of the cavity 114, heart implant 120, and plug 130. FIG. 3A shows the heart implant 120 removed from the cavity 114 and detached from the elongate body 108. The cable 112 is retracted within the lumen 110 of the elongate body 108 so as to be positioned proximally of a proximal end of the cavity 114. The cable 112 is typically moved to this position via detachment of the cable deployment mechanism 208 from the plunger 206. FIG. 3B illustrates the heart implant 120 positioned within the cavity 114 with the heart implant's lumen 124 substantially axially aligned within an axis of the cavity 114 and the elongate body 108. The cable 112 is inserted through the lumen 124 of the heart implant 120, which temporarily couples the heart implant 120 with the elongate body 108. The distal tip of the elongate body 108 is capped, plugged, or otherwise closed via the plug 130 to prevent the cable 112 from extending distally beyond the elongate body 108. The distal tip of the cable 112 is directly adjacent, or in contact with, the plug 130 as illustrated.

Since the cable 112 is positioned internally within the elongate body 108, both proximally and distally of the heart implant 120 and cavity 114, the heart implant 120 is essentially locked or restrained within the cavity 114, which prevents accidental or undesired uncoupling or detachment of these components. An inner surface of the heart implant 120 is in direct contact with the interior of the elongate body 108 while the heart implant 120 remains exposed to the surrounding environment, which in use is typically the interior of the heart chamber.

The cavity 114 is sized slightly larger than the heart implant 120. For example, the cavity 114 has a longitudinal dimension X which is slightly greater than the longitudinal length Y of the heart implant 120. The cavity 114 should be dimensioned so that the heart implant may be easily aligned and coupled with the cavity 114 and so that the cable 112 is able to flex or deploy outward from the cavity 114 in response to distal sliding of the cable 112 within the lumen 110 of the elongate body 108. Stated differently, the cavity 114 should not be dimensioned so that it prevents or greatly restricts the cable 112 from flexing or deploying outward from the cavity 114, which may occur if the cavity 114 is similar in size to the longitudinal length of the heart implant 120.

The tether 122 is shown extending distally from the heart implant 120 and elongate body 108. The tether 122 may be inserted within the vasculature and heart chamber distally of the heart implant 120 and elongate body 108 and may be used to guide or direct the heart implant 120 and elongate body 108 through the vasculature and within the heart chamber. The tether 122 is pivotally attached or coupled with the heart implant 120 so that the implant is able to pivot about the end of the tether 122.

FIG. 3C illustrates the cable 112 being used to initially deploy or pivot the heart implant 120 from the cavity 114 of the elongate body 108. The cable 112 is designed to flex, buckle, or bend in response to an operation of the handle 106 and specifically, the distal movement of the grip member 202 within the elongate slot 212 of the main body 200. Distal movement of the grip member 202 causes the plunger 206 to slide distally within the main body 200, which causes a corresponding distal sliding of the cable 112 within the lumen 110 of the elongate body 108. The plug 130 prevents the cable from extending or sliding distally of the distal tip of the elongate body 108, which causes the cable 112 to buckle and bend or flex outward from the cavity 114 as illustrated. Because the cable 112 is disposed within the lumen 124 of the heart implant 120, outward flexing or bending of the cable 112 causes the heart implant to pivot, move, or deploy outward from the cavity 114. The buckling of the cable 112 may also cause the distal end of the elongate body 108 to flex or bend in an opposite direction as illustrated in FIG. 3C. This flexing or bending of the elongate body 108 may be controlled by increasing or decreasing the thickness of the elongate body's material strip that extends across the cavity 114.

Proximal movement of the grip member 202 causes the plunger 206 to slide proximally within the main body 200, which causes a corresponding proximal sliding of the cable 112 within the lumen 110 of the elongate body 108. This retracts the cable 112 within the lumen 110 of the elongate body, which causes the heart implant 120 to pivot or move back into the cavity 114. When the heart implant 120 is retracted within the cavity 114, the lumen 124 is typically realigned with the axis of the cavity 114 and elongate body 108. In this manner, the heart implant 120 may be initially deployed from and retracted within the cavity 114. The heart implant 120 may also be permanently deployed form the cavity 114 by detaching the cable deployment mechanism 208 from the plunger 206.

While FIGS. 3A-C illustrate the elongate body 108 including the plug 130, in other embodiments the elongate body 108 may be configured so that the lumen 110 terminates or stops short of the distal end of the elongate body 108 and therefore, does not extend fully through the distal end of the elongate body 108. In yet other embodiments, the distal tip of the elongate body 108 may be pinched or formed together to plug, cap, or otherwise close the lumen 110 and thereby prevent the cable 112 from extending distally of the elongate body's distal tip.

Figure 4A:
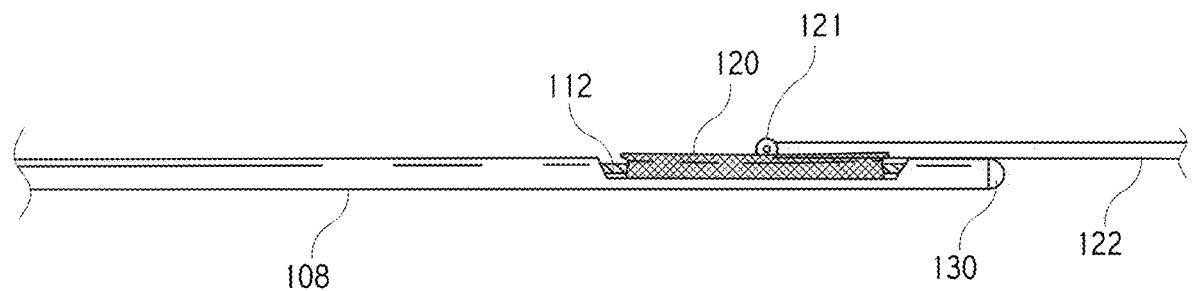
FIGS. 4A-B illustrate a deployment of a heart implant from a cavity of the distal end of the heart implant alignment and delivery device.
Figure 4B:
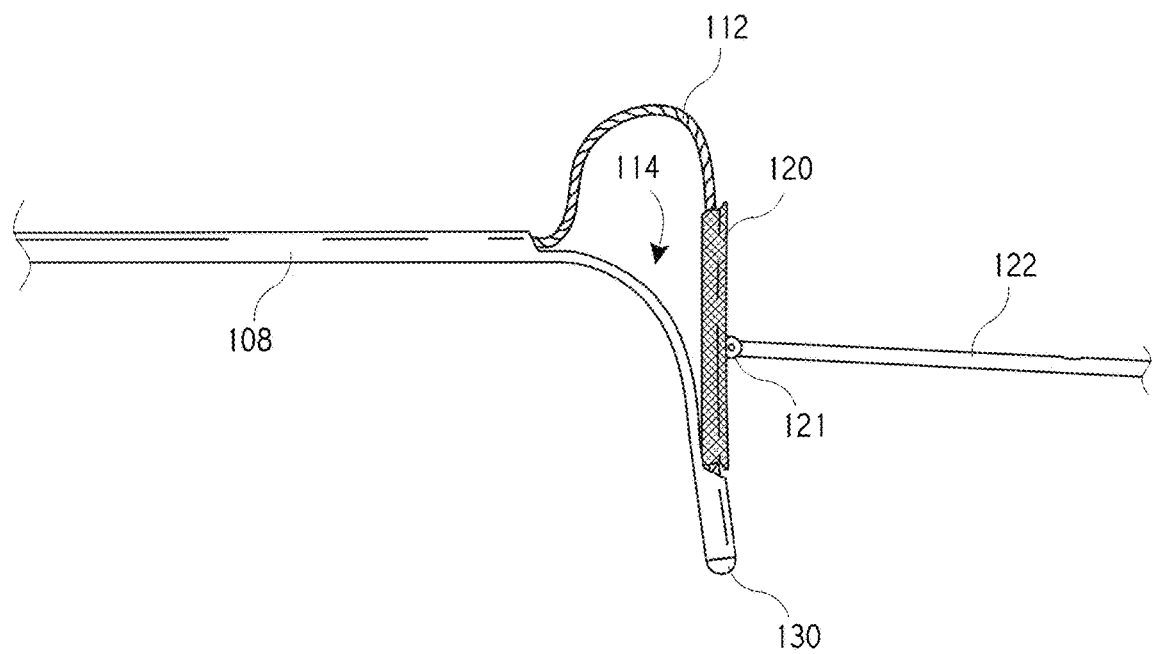

FIGS. 4A-B illustrate the deployment of the heart implant 120 from the cavity 114 of the elongate body 108. As described herein, the heart implant 120 is deployed via operation of the cable 112. Prior to deployment of the heart implant 120, the heart implant 120 may be aligned with the cable 112 and elongate body 108 as illustrated in FIG. 4A. The heart implant 120 may be deployed from the cavity 114 in a pivot-like manner or fashion. Since the tether 122 is connected to the heart implant 120 via a pivot joint 121, the sliding of the cable 112 causes the heart implant 120 to pivot or flex about the pivot joint 121. The bowing or flexing of the cable 112 may also cause the distal portion or end of the elongate body 108 to bow or flex in an opposite direction as shown. The heart implant 120 may be deployed or pivoted relative to the elongate body 108 so that the heart implant 120 is roughly orthogonal to an axis of proximal portion of the elongate body 108 as illustrated.

Figure 5A:
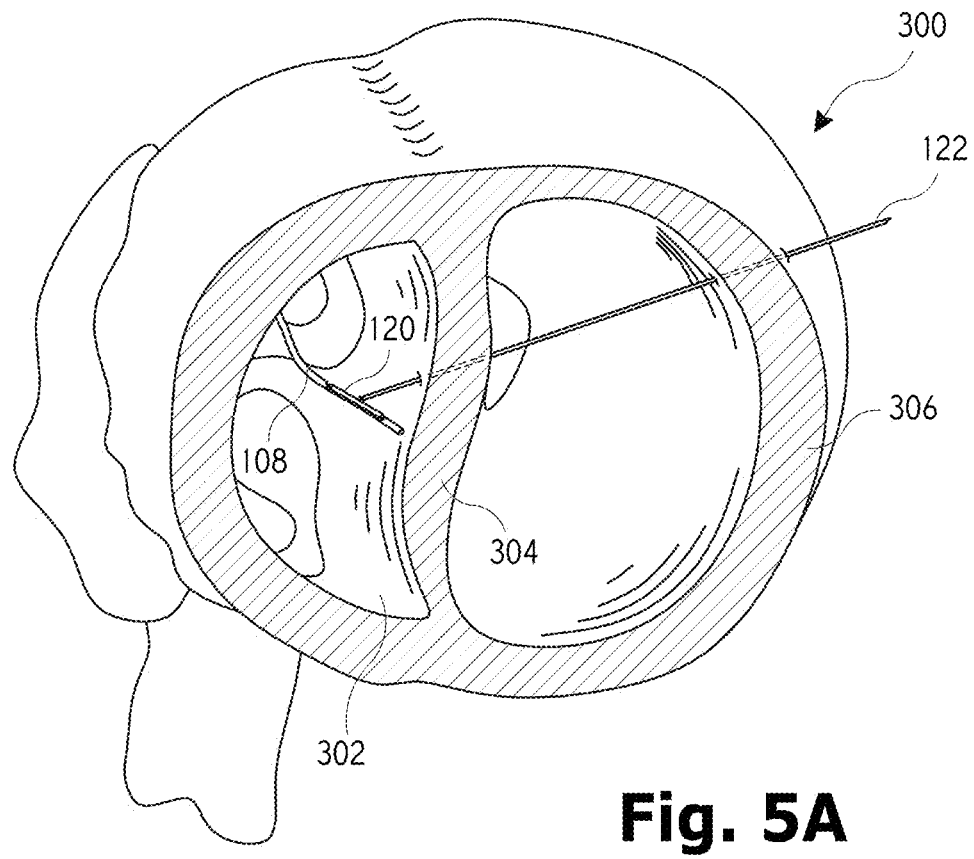
FIGS. 5A-C illustrate a method of deploying a heart implant from the heart implant alignment and delivery device and within a chamber of a heart.
Figure 5B:
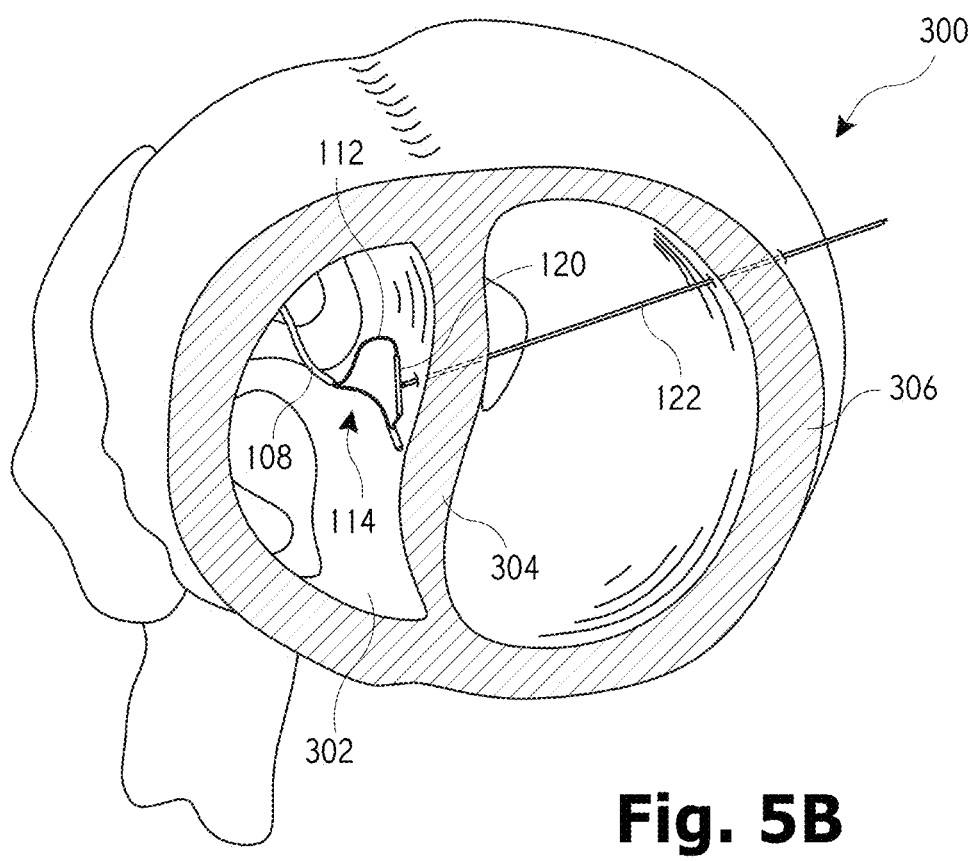
Figure 5C:
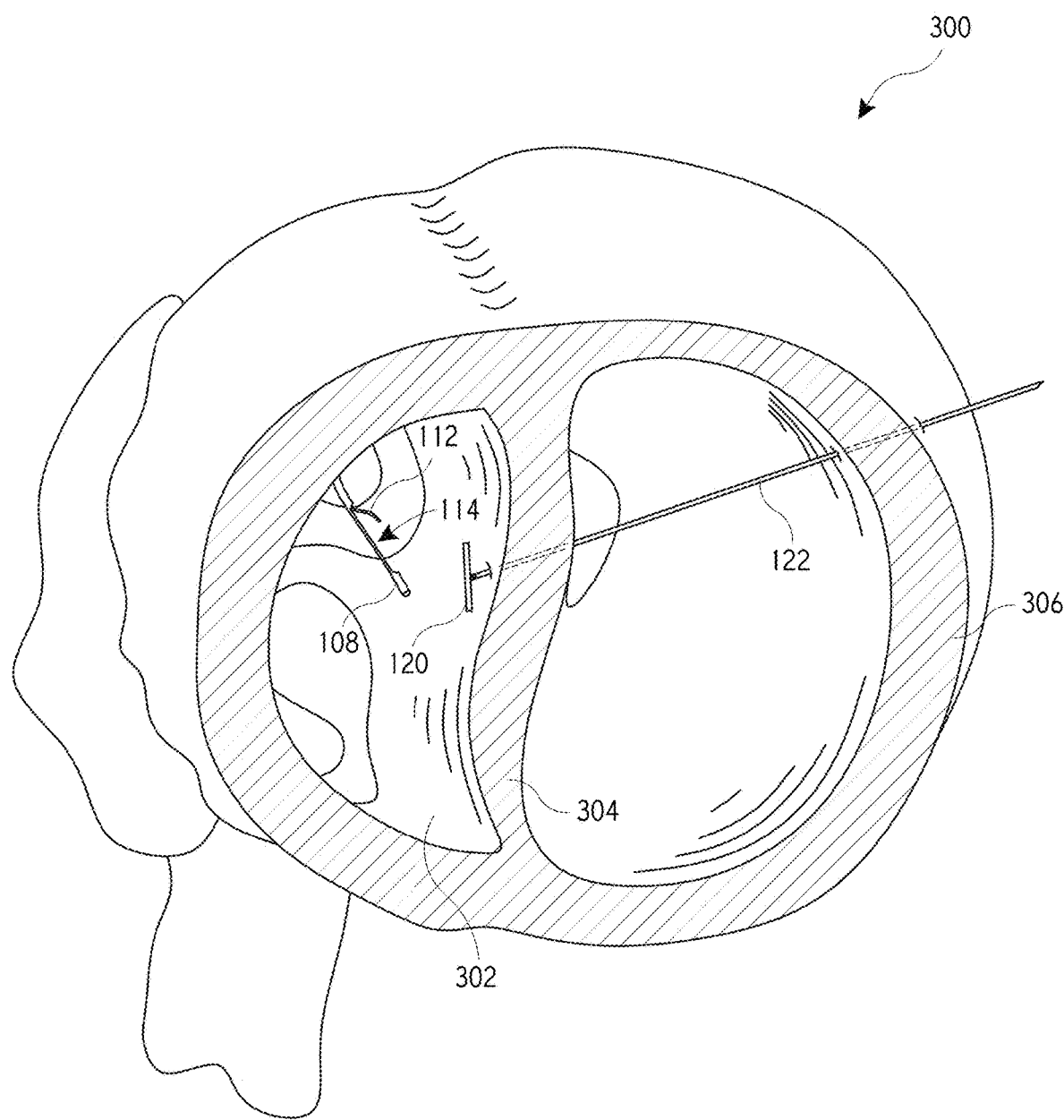

FIGS. 5A-C illustrates a method of deploying the heart implant 120 from the catheter 100 and within a chamber 302 (e.g., left ventricle) of a heart 300. In FIG. 5A, the distal end of the elongate body 108 is positioned within the chamber 302 of the heart 100 so that the cavity 114 and heart implant 120 are positioned near or adjacent a septum 304 of the heart 300. The tether 122 extends from the heart implant 120 and through the septum 304 and an exterior wall 306 of the heart. The tether 122 may extend distally therefrom and through an incision within the patient's body, such as through an incision between the patient's ribs.

In FIG. 3B, a first operation of the handle 106 is performed to cause the cable 112 to flex, buckle, or bend outward from the cavity 114 of the elongate body 108 and thereby cause the heart implant 120 to pivot out of the cavity 114. In some instances, the heart implant 120 may pivot into contact with the septum 304. As described herein, the first operation of the handle 106 may be a distal sliding of the grip member 202 within the elongate slot 212 of the handle's main body 200. The heart implant 120 is retractable within the cavity 114 to enable repositioning of the elongate body 108 within the heart 300 and thereby ensure a proper alignment of the heart implant 120 relative to the wall 304 of the heart 300. For example, with the heart implant 120 pivoted or deployed from the cavity 114, a physician may assess if the heart implant 120 is properly aligned or oriented about the septum 304 to provide a desired therapeutic treatment, such as closing off a desired portion of the right ventricle.

If the heart implant 120 is not properly aligned or oriented about the septum 304, then the heart implant 120 may be retracted within the cavity 114. Specifically, a second operation of the handle 106 may be performed to cause the cable 112 to retract within the lumen 110 of the elongate body 108 and thereby cause the heart implant 120 to retract into the cavity 114. The heart implant 120 is then repositionable within the chamber 302 of the heart 300 after retraction of the cable 112 and heart implant 120. As described herein, the second operation of the handle 106 may be a proximal sliding of the grip member 202 within the elongate slot 212 of the handle's main body 200.

The elongate body 108 and heart implant 120 may be repositioned within the chamber 302 of the heart 300 so that the heart implant 120 is repositioned relative to the septum 304. The first operation of the handle 106 (i.e., distal sliding of the grip member 202) may then be performed again to cause the cable 112 and heart implant 120 to flex or pivot outward from the cavity 114 so that the physician can assess the new position of the heart implant 120 relative to the septum 304.

As illustrated in FIG. 5C, upon a determination that the alignment or orientation of the heart implant 120 is proper relative to the septum 304, a third operation of the handle 106 may be performed to permanently deploy the heart implant 120 from the cavity 114 of the elongate body 108. As described herein, the third operation of the handle 106 may involve detaching the cable deployment mechanism 208 from the plunger 206 of the handle 106 and/or pulling the cable deployment mechanism 208 proximally of the plunger 206. Once the heart implant 120 is detached from the cavity 114 and elongate body 108, the elongate body 108 may be removed from the chamber 302 of the heart 300 and from the patient's body. As further described in the various U.S. applications incorporated herein, the heart implant 120 and tether 122 may then be used to apply tension to the septum 304 and exterior wall 306 for various reasons including bringing the inner surfaces of the walls, 304 and 306, into engagement. The heart implant 120 and tether 122 may also be used to permanently affix the septum 304 and exterior wall 306 in a desired orientation, such as by affixing an epicardial anchor (not shown) to the tether 122.

Deployment of the heart implant 120 via the cable 112 allows the physician to have improved control over positioning of the heart implant 120 against the heart wall. For example, if the heart implant 120 needs to be rotated relative to the heart wall, the cable 112 may be retracted proximally to cause the heart implant 120 to be repositioned within the cavity 114 and the catheter 100 and elongate body 108 may be rotated to cause the heart implant 120 to be moved rotationally relative to the heart wall. The heart implant 120 may then be redeployed into contact with the heart wall via the process described herein. Similarly, if the heart implant 120 is contacting, entangling, or otherwise engaging with internal heart structures during deployment, the cable 112 may be retracted proximally to reposition the heart implant 120 within the cavity 114. The heart implant 120 and/or elongate body 108 may then be rotated to reposition the heart implant 120 relative to the heart to a position where it is less likely that the heart implant 120 will contact, entangle, or engage with heart structures during deployment. The heart implant 120 may then be redeployed against the heart wall using the cable 112 and handle 106.

The use of the cable 112 further prevents or minimizes unnecessary and potentially problematic movement of the heart implant 120 at the distal end of the tether 122. For example, if the heart implant 120 is able to freely pivot or move at or about the distal end of the tether 122, the heart implant 120 may be prone to contacting and engaging with the heart tissue (e.g., Chordae, Papillary Leaflets, Tricuspid Valve, etc.). The use of the cable 112 prevents or minimizes free pivoting or movement of the heart implant 120 about the distal end of the tether 122.

Figure 6:
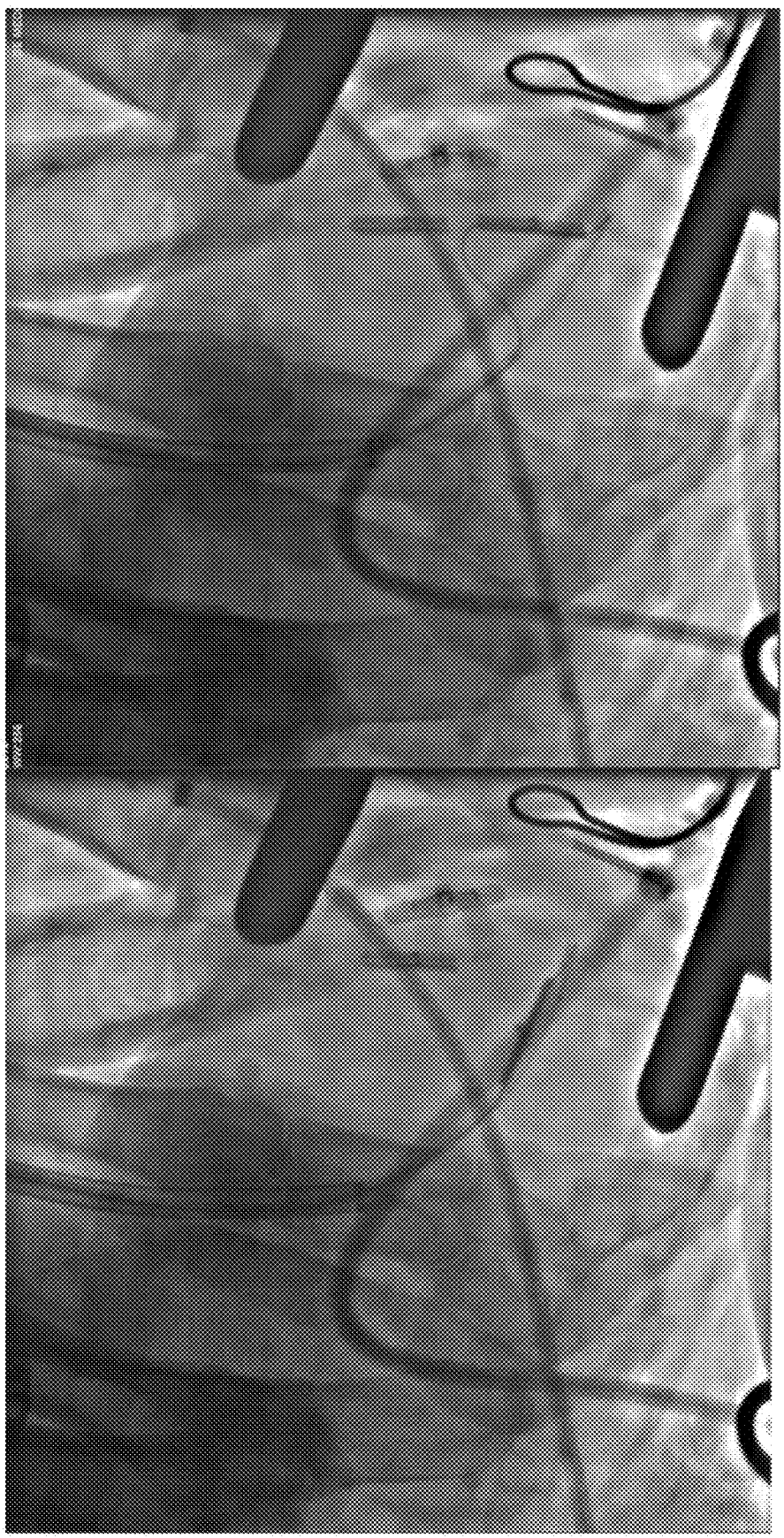
FIG. 6 illustrates an image of a heart implant being positioned within a right ventricle of an animal.

FIG. 6 illustrates an image of a heart implant or anchor being positioned within a right ventricle of an animal. The left hand image shows the heart implant or anchor in an un-deployed or insertion position where an axis of the heart implant or anchor is aligned with the axis of the elongate body. The right hand image shows the heart implant or anchor being deployed or pivoted from the elongate body's cavity or anchor window and into contact with the inner surface of the right ventricle via the cable. The heart implant or anchor rests against the septum of the heart subsequent to deployment of the anchor.

While several embodiments and arrangements of various components are described herein, it should be understood that the various components and/or combination of components described in the various embodiments may be modified, rearranged, changed, adjusted, and the like. For example, the arrangement of components in any of the described embodiments may be adjusted or rearranged and/or the various described components may be employed in any of the embodiments in which they are not currently described or employed. As such, it should be realized that the various embodiments are not limited to the specific arrangement and/or component structures described herein.

In addition, it is to be understood that any workable combination of the features and elements disclosed herein is also considered to be disclosed. Additionally, any time a feature is not discussed with regard in an embodiment in this disclosure, a person of skill in the art is hereby put on notice that some embodiments of the invention may implicitly and specifically exclude such features, thereby providing support for negative claim limitations.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A catheter for delivering and aligning a heart implant about a wall of a heart, the catheter comprising:
    an elongate body;
    a lumen disposed through the elongate body;
    an opening formed within a distal end of the elongate body; and
    a cable positioned within the lumen of the elongate body so that the cable is slidably positioned on a proximal side of the opening and on a distal side of the opening;
    wherein:
        the cable is releasably coupleable with the heart implant;
        the cable is slideable within the lumen of the elongate body; and
        the catheter is configured so that a distal advancement the cable within the lumen causes the cable to pivot or flex outward through the opening.

2. The catheter of claim 1, wherein a distal end of the cable is confined within the distal end of the elongate body such that sliding the cable distally within the lumen causes the cable to pivot or flex outward through the opening.

3. The catheter of claim 2, wherein a portion of the cable that is proximal of a distal end of the cable pivots or flexes outward through the opening as the cable is slid distally within the lumen.

4. The catheter of claim 2, wherein prior to sliding the cable distally within the lumen, the cable is coaxially aligned with the elongate body, and wherein subsequent to sliding the cable distally within the lumen, a portion of the cable is not coaxially aligned with the elongate body.

5. The catheter of claim 2, wherein the cable is retractable within the opening.

6. The catheter of claim 2, wherein the distal end of the elongate body is capped so that the lumen terminates at the distal end of the elongate body and so that the distal end of the cable is confined within the distal end of the elongate body.

7. The catheter of claim 1, wherein the heart implant is permanently releasable from the cable and from the catheter.

8. The catheter of claim 7, wherein the cable is slideably positionable through a lumen of the heart implant, and wherein the cable is retractable proximally of a proximal end of the heart implant to permanently release the heart implant from the cable.

9. A catheter for delivering a heart implant, the catheter comprising:
an elongate body;
a lumen disposed through the elongate body;
an opening within a distal end of the elongate body; and
a cable positioned within the lumen of the elongate body so that the cable is slideable within the lumen of the elongate body;
wherein a distal end of the cable is confined within a distal end of the elongate body so that sliding the cable distally within the lumen causes the cable to pivot or flex outward through the opening; and
wherein the cable is retractable within the lumen of the catheter while the distal end of the cable is coaxially aligned with the lumen.

10. A method of deploying a heart implant from a catheter, the catheter including an elongate body having a cylindrical wall, a lumen disposed through the elongate body, an opening formed in the cylindrical wall, and a cable disposed within the lumen and operably coupled with the heart implant, the method comprising:
positioning a distal end of the elongate body within a chamber of a heart so that the opening of the catheter is adjacent a wall of the heart;
advancing the cable distally within the lumen to cause the cable and heart anchor to pivot or flex outward through the opening; and
retracting the cable proximally within the lumen of the elongate body while a distal end of the cable is coaxially aligned with the lumen;
wherein the catheter is configured so that a distal movement of the distal end of the cable is confined such that distally advancing the cable within the lumen causes the cable to pivot or flex outward through the opening.

11. The method of claim 10, wherein the heart implant is retractable within the opening to enable repositioning of the elongate body within the heart and thereby enable a proper alignment of the heart implant relative to the wall of the heart.

12. The method of claim 11, further comprising retracting the cable proximally within the lumen of the elongate body to cause the cable and heart implant to retract within the opening.

13. The method of claim 12, wherein the cable is retractable within the lumen of the elongate body so that a distal tip of the cable is positioned proximally of a proximal end of the opening.

14. The method of claim 13, wherein the cable is slideably disposed through a lumen of the heart implant, and wherein retracting the cable proximally of the proximal end of the opening releases the heart implant from the cable.

15. The method of claim 12, further comprising:
repositioning the distal end of the elongate body within the chamber of the heart so that the opening of the catheter is repositioned about the wall of the heart; and
advancing the cable distally to cause the cable and heart implant to pivot or flex outward from the opening.

16. The method of claim 15, further comprising permanently deploying the heart implant from the catheter.

17. The method of claim 10, wherein the heart implant is pivotably coupled with a tension member.

18. The method of claim 10, wherein the opening is a channel that is formed in the cylindrical wall of the catheter, wherein the channel has a length corresponding to a length of the heart implant.

19. The method of claim 10, wherein a distal end of the elongate body is capped so that the lumen terminates at the distal end of the elongate body and so that the distal end of the cable is confined within the distal end of the elongate body.

* * * * *